United States Patent [19]

Spector

[11] Patent Number: 4,493,011
[45] Date of Patent: Jan. 8, 1985

[54] AROMA DISC FOR TABLE LAMP

[76] Inventor: Donald Spector, 380 Mountain Rd., Union City, N.J. 07087

[21] Appl. No.: 589,465

[22] Filed: Mar. 14, 1984

[51] Int. Cl.³ .............................................. A61L 9/02
[52] U.S. Cl. ..................................... 362/96; 362/101; 362/414; 362/417; 239/56; 428/65; 428/137; 428/905
[58] Field of Search .................... 428/905, 28, 65, 131, 428/137; 422/125; 362/96, 101, 414, 417; 239/34, 56, 57

[56] References Cited

U.S. PATENT DOCUMENTS

| | | | |
|---|---|---|---|
| 1,403,548 | 1/1922 | Gudeman | 239/34 X |
| 2,372,371 | 3/1945 | Eisner | 239/34 X |
| 2,419,357 | 4/1947 | Krasner et al. | 428/137 X |
| 2,435,756 | 2/1948 | Schlesinger | 239/34 X |
| 2,557,501 | 6/1951 | Fusay et al. | 239/34 X |
| 3,084,624 | 4/1963 | Cheshire | 101/22 X |
| 3,784,102 | 1/1974 | Stults | 239/57 X |
| 4,009,384 | 2/1977 | Holland | 428/905 X |
| 4,167,034 | 9/1979 | Noguchi | 362/417 X |
| 4,283,011 | 8/1981 | Spector | 239/57 X |
| 4,346,059 | 8/1982 | Spector | 239/34 X |

Primary Examiner—Henry F. Epstein
Attorney, Agent, or Firm—Michael Ebert

[57] ABSTRACT

An aroma disc usable in conjunction with a conventional table lamp whose light bulb socket has a harp secured thereto to support a lampshade, the harp being provided with an upwardly projecting bolt on which is received the center collar of the lampshade spider. The aroma disc includes a round pad of porous material impregnated with a liquid fragrance, the pad being sandwiched between two round plies of reflective metal which are peripherally joined together and are provided with a center hole to accommodate the harp bolt whereby when the disc is installed on the lamp it is placed above the bulb. Concentric with the center hole on each ply of the disc is a circular array of openings which define ports to expose the pad. When the lamp is turned on, heated air currents arising from the bulb penetrate the ports and pass through the pad to volatilize the liquid fragrance, thereby generating an aromatic vapor which suffuses the room illuminated by the lamp.

6 Claims, 4 Drawing Figures

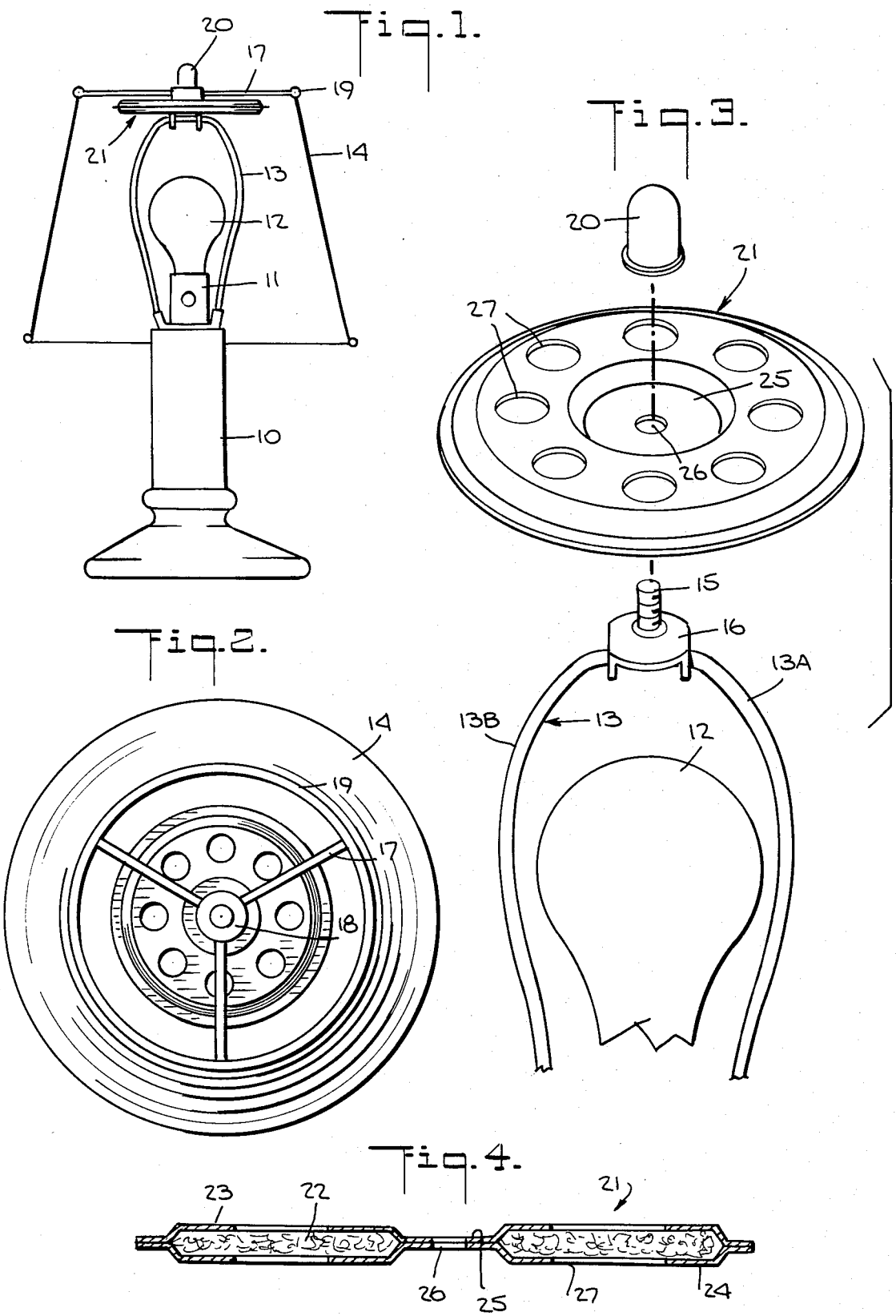

AROMA DISC FOR TABLE LAMP

BACKGROUND OF INVENTION

Field of Invention

This invention generally relates to aroma generators, and more particularly to an aroma disc which is attachable to a table lamp and which, when the lamp is turned on, generates an aromatic vapor.

As used herein, the term "aroma" is not limited to pleasant or savory smells, but encompasses scents that function as insecticides, air fresheners, deodorants or any other odor that acts to condition, modify or otherwise charge the atmosphere. With an aroma disc in accordance with the invention, one has a choice of discs to be used in conjunction with the table lamp, the selection depending on the atmospheric effect to be created.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol.

It is known to promote vaporization of aroma-producing liquids by means of a heat-generating electric light bulb. Thus the Eisner U.S. Pat. No. 2,372,371 shows a pad saturated with a deodorant held in a small container mounted directly on the bulb. Similar bulb arrangements to promote vaporization are disclosed in the Gudeman U.S. Pat. No. 1,403,548; the Fusay et al. U.S. Pat. No. 2,557,501; the Schlesinger U.S. Pat. No. 2,435,756; and the Weber U.S. Pat. No. 3,084,624.

In my prior U.S. Pat. No. 4,346,059 there is disclosed an aroma generator in which a pad of porous material impregnated with an aroma-producing liquid is disposed under a vent in a substantially enclosed housing. An electrical heating element placed in the housing acts to heat and expand the air confined therein to create a positive air pressure producing a pressure differential between the heated air and the atmosphere above the vent, as a consequence of which the heated air is driven through the pad to rapidly volatilize the liquid and exude an aromatic vapor through the vent into the atmosphere.

In my above-identified copending application there is disclosed an aroma disc for use in a player whereby when the disc is inserted therein, an aromatic vapor is then discharged into the atmosphere. In this arrangement, the disc is formed by a circular sheet of absorbent material impregnated with a liquid fragrance and sandwiched between a pair of annular plastic films which are peripherally joined to create a central zone exposing the impregnated sheet. In the player, heated air under positive pressure is forced through the central zone to volatilize the liquid to produce an aromatic vapor which is discharged through vents in the casing of the player.

The concern of the present invention is with aroma discs for use in conjunction with table lamps. A conventional table lamp includes a light bulb socket mounted on an upright base. The socket has a harp secured thereto provided with an upwardly projecting bolt for supporting a lamp shade having a spider whose center collar is received in the bolt, the bulb being encaged by the harp. The present invention is usable with lampshade harps of the type disclosed in the Noguchi U.S. Pat. No. 4,167,034.

A table lamp is normally turned on only when the room in which it is placed is occupied, the occupant switching on the lamp. And it is only when the room is occupied that a need arises for an aroma generator to modify or freshen the atmosphere of the room. In the absence of an occupant, should the roma generator or air freshener, such as the well known "Air-Wick" air freshener, be active, then the limited supply of liquid fragrance or whatever other aromatic substance is being used, would gradually become depleted, so that it may not be available when the need for an aromatic vapor arises. Thus if an air freshener is active all night when the room is unoccupied, though it serves no useful purpose, it is then being discharged.

SUMMARY OF INVENTION

In view of the foregoing, the main object of this invention is to provide an aroma disc usable in conjunction with a conventional table lamp, the disc being rendered effectively operative only when the lamp is turned on, thereby conserving the available supply of aromatic liquid.

More particularly, an object of this invention is to provide an aroma disc which is attachable to the table lamp in the same manner as a standard lampshade, the disc, when installed, being placed as a canopy over the bulb and serving not only to generate an aromatic vapor but also to reflect light from the bulb downwardly to render the table lamp more effective as a source of illumination.

A table lamp, as distinguished from an overhead light source, is intended to illuminate only a limited region of the room. Thus a table lamp placed on a table adjacent a reading chair serves mainly to provide light for the occupant of the chair. Since the standard lampshade is open on the top, the light radiating upward from the light bulb passes through the open top and is largely wasted. A significant feature of the present invention is that the aroma disc also functions as a reflector to direct light rays from the light bulb downwardly where they serve a more useful purpose.

Also an object of the invention is to provide an aroma disc which is adapted for ready attachment to a table lamp whereby when the disc is exhausted, it may be replaced without difficulty with a fresh aroma disc having the same or a different aroma.

Thus another advantage of the invention is that the environment of a room may be modified in a manner appropriate to the occasion, so that the aroma disc used during, say, an Xmas celebration, may be one exuding the aroma of pine trees; whereas when the room is filled with tobacco smoke, an air freshener disc may then be put in place.

Also an object of this invention is to provide an aroma disc that may be mass-produced at low cost.

Briefly stated, these objects are attained in an aroma disc usable in conjunction with a conventional table lamp whose light bulb socket has a harp secured thereto to support a lampshade, the harp being provided with an upwardly projecting bolt on which is received the center collar of the lampshade spider. The aroma disc includes a round pad of porous material impregnated with a liquid fragrance, the pad being sandwiched between two round plies of reflective metal which are peripherally joined together and are provided with a center hole to accommodate the harp bolt whereby when the disc is installed on the lamp it is placed above the bulb. Concentric with the center hole on each ply of the disc is a circular array of openings which define ports to expose the pad. When the lamp is turned on, heated air currents arising from the bulb penetrate the ports and pass through the pad to volatilize the liquid fragrance, thereby generating an aromatic vapor which suffuses the room illuminated by the lamp.

OUTLINE OF DRAWINGS

For a better understanding of the invention as well as other objects and further features, thereof, reference is made to the following detailed description to be read in conjunction with the accompanying drawings, wherein:

FIG. 1 shows, in perspective, a standard table lamp having attached thereto an aroma disc in accordance with the invention;

FIG. 2 is a top view of the table lamp;

FIG. 3 is an exploded view showing the aroma disc, the light bulb harp and the aroma disc to be attached thereto; and FIG. 4 is a diametrical section taken through the disc.

DESCRIPTION OF INVENTION

Referring now to FIG. 1, there is shown a standard table lamp comprising an upright base 10, an electrical socket 11 mounted on top of the base for receiving an incandescent light bulb 12, and a harp 13 secured to the socket for supporting a light shade 14.

As shown in FIG. 3, harp 13 is composed of a pair of curved metal arms 13A and 13B on opposite sides of bulb 12, and an upright threaded bolt 15 secured to the top center of the harp by a bolt anchor 16. The lampshade 14, as best seen in FIG. 2, includes a spider 17 whose arms radiate from a center collar 18 to the circular rim 19 of the lampshade. Collar 18 fits over bolt 15 and is held thereto by a nut head 20. Thus it is a simple matter to seat the lampshade on the lamp, for one has only to fit the collar of the spider on the bolt 15 and then turn the nut head 20 on the bolt to tighten the lampshade in place.

The invention is not limited to use with the table lamp shown and is applicable to any lamp structure in which the harp which encages the lamp is provided with an upright bolt.

Also supported on bolt 15 is an aroma disc 21 which overlies the radial arms of spider 17 and is coaxial with the rim 19 of the lampshade, the disc partially blocking the normally open top of the lampshade.

Aroma disc 21, as shown in FIGS. 3 and 4, is constituted by a round pad 22 of absorbent material having good wicking properties, the pad being sandwiched between two round plies 23 and 24 of reflective metal, such as thin sheets of aluminum or brass. In practice, instead of metal, the plies may be formed of plastic sheeting having a metallized surface. Pad 22 may be fabricated of blotting paper, non-woven textured fabric, flexible open-cell foam plastic material or any other absorbent material which is non-reactive with the aromatic liquid that is used.

The metal plies 23 and 24 are joined together at their peripheries, as by crimping or by folding the peripheral margin of one ply over the other to provide a peripheral seal which also rigidifies the disc. The central zones of the two plies are embossed inwardly to define a depressed circular hub 25 within which the pad is compressed. Hub 25 is provided with a center bore 26 to accommodate the harp bolt 15. Both plies are provided with a circular array of openings concentric with bore 26 to define a series of small ports 27 which expose pad 22. In practice, the cutting of the ports and embossing of the metal plies may be carried out in a die.

After the roma disc is assembled, a liquid fragrance is added to the absorbent pad through one or more of ports 27. Thus, one may even immerse the assembly in a bath of liquid fragrance. Because of the wicking properties of the pad, the liquid, though introduced through the ports, is uniformly dispersed throughout the entire body of the pad, only a portion of which is exposed by the ports. In this way, the pad provides a substantial supply of liquid fragrance. In practice, the aroma disc may be stored in a sealed plastic or foil envelope to conserve the liquid supply until such time as the disc is put in place in a lamp.

When the disc is mounted on bolt 15 below the spider of the lampshade as shown in FIG. 2, under normal room conditions, very little fragrance is emitted from the disc with the lamp turned off. Volatilization of the liquid fragrance takes place at a rate determined by the termperature of air to which the disc is subjected and the rate of air flow. When the lamp is turned off, the air is at room temperature and there is little convection; hence volatilization is at a very low level. But when the lamp is turned on, the air in the vicinity of the lamp is heated by the incandescent bulb and the rising hot air currents are blocked by the aroma disc; for these currents can only pass through the open top of the lampshade.

As a consequence, a positive air pressure is created under the aroma disc, causing the hot air currents to force their way through the ports of the aroma disc to penetrate the liquid-impregnated pad, thereby volatilizing the liquid to provide an aromatic vapor which suffuses the room in which the lamp is placed. And because the aroma disc lies on top of the lampshade spider, it is inconspicuous, and occupants of the room are not therefore aware of the source of the aroma.

Since the aroma disc is activated only when the lamp is turned on, this conserves the liquid fragrance supply; for in the absence of room occupants, the lamp is normally turned off and there is no need for aromatic modification of the atmosphere.

And because the aroma disc is formed of reflective material, it serves to downwardly direct light ways emerging from the bulb. Since the lamp is not intended to illuminate the ceiling of the room but only the region in the vicinity of the lamp, the aroma disc renders the lamp more effective for its intended purpose.

While there has been shown and described a preferred embodiment of an aroma disc for table lamp in accordance with the invention, it will be appreciated that many changes and modifications may be made therein without, however, departing from the essential spirit thereof. Thus, the center hole of the disc may be made oversize so that the disc, instead of being under the head nut, accommodates the head nut and simply lies on the spider of the lampshade.

I claim:

1. An aroma disc usable in conjunction with a conventional table lamp whose light bulb socket has a harp secured thereto to support a lampshade having a spider provided with a center collar, the harp being provided with an upright bolt to receive the collar, said disc comprising:
- A. a round pad of porous material having good wicking properties and impregnated with a liquid fragrance; and
- B. a pair of round plies on opposite faces of the pad, the plies being joined peripherally to form a disc having a peripheral seal which also rigidifies the disc, said disc having a center hole to accommodate said bolt, said plies having a circular array of openings therein concentric with the center hole to define ports for directly exposing the pad in the port regions thereof, whereby when the lamp is turned on, the resultant hot air currents penetrate the ports to volatilize the liquid fragrance to generate an aromatic vapor, the portions of the pad surrounding the port regions acting as a reservoir for the liquid fragrance which is wicked into the port regions as the liquid fragrance is volatilized.

2. An aroma disc as set forth in claim 1, wherein said pad is formed of porous paper.

3. An aromatic disc as set forth in claim 1, wherein said plies are formed of sheet metal.

4. An aromatic disc as set forth in claim 3, wherein said metal has a reflective surface.

5. An aroma disc as set forth in claim 1, wherein said disc has a depressed hub zone surrounding the center hole.

6. An aroma disc as set forth in claim 1, wherein said collar is locked by a head nut received on said bolt and said center hole is large enough to fit over the head nut.

* * * * *